(12) United States Patent
Shah

(10) Patent No.: US 6,723,098 B1
(45) Date of Patent: Apr. 20, 2004

(54) BONE FIXATION PLATE HAVING CLIP MEMBERS

(76) Inventor: Mrugesh K. Shah, 403 Trails Ct., Houston, TX (US) 77024

( * ) Notice: Subject to any disclaimer, the term of this patent is extended or adjusted under 35 U.S.C. 154(b) by 88 days.

(21) Appl. No.: 10/094,868

(22) Filed: Mar. 12, 2002

(51) Int. Cl.[7] ............................................... A61B 17/56
(52) U.S. Cl. ...................................................... 606/71
(58) Field of Search ............................. 606/61, 69, 70, 606/71

(56) References Cited

U.S. PATENT DOCUMENTS

| | | | |
|---|---|---|---|
| 2,443,363 A | 6/1948 | Townsend et al. | |
| 2,486,303 A | 10/1949 | Longfellow | |
| 3,534,731 A | * 10/1970 | Muller | 606/105 |
| 3,604,414 A | 9/1971 | Borges | |
| 3,659,595 A | 5/1972 | Haboush | |
| 3,695,259 A | * 10/1972 | Yost | 606/69 |
| 4,957,497 A | 9/1990 | Hoogland et al. | |
| 5,234,431 A | 8/1993 | Keller | |
| 5,364,398 A | * 11/1994 | Chapman et al. | 606/69 |
| 5,665,089 A | * 9/1997 | Dall et al. | 606/71 |
| 5,735,853 A | * 4/1998 | Olerud | 606/71 |
| 5,741,258 A | * 4/1998 | Klaue et al. | 606/70 |
| 5,951,557 A | 9/1999 | Luter | |
| 6,280,445 B1 | 8/2001 | Morrison | |
| 6,322,562 B1 | * 11/2001 | Wolter | 606/69 |
| 2001/0037112 A1 | * 11/2001 | Brace et al. | 606/69 |

* cited by examiner

*Primary Examiner*—Eduardo C. Robert
(74) *Attorney, Agent, or Firm*—Harrison & Egbert

(57) ABSTRACT

A bone fixation plate including a plate having a first set of openings and a second set of openings, and a plurality of clip members removably fitted within the respective opening of the second set of openings. The first set of openings include a plurality of circular through holes. The second set of opening includes a plurality of elongated holes extending through the plate transverse to the longitudinal axis of the plate. Screws are fitted through the first set of openings and the second set of openings so as to engage bone portions on opposite sides of a break.

19 Claims, 2 Drawing Sheets

BONE FIXATION PLATE HAVING CLIP MEMBERS

BACKGROUND OF THE INVENTION

1. Field of the Invention

The present invention relates to generally to orthopaedic implants and more particularly, to bone plates and bone plate assemblies that may be implanted in various parts of the human body to stabilize bone fractures.

2. Description of Related Art

Orthopaedic surgeons frequently encounter bone fractures which require surgical stabilization with implants including metal bone plates having a variety of shapes. Difficulties in the repair of these fractures include insufficient assistance in the operating theater and fractures that are difficult to reduce (i.e., returning the fractured bone segments to their proper positions) and hold. Conventional bone plates may be generally classified as either "compression plates" or "one-third semi-tubular plates." Both types of plates are available in a variety of shapes, for use in stabilizing various bones, and typically include a plurality of interior holes (i.e., spaced apart from the edge of the plate and surrounded by metal) which accept bone screws to secure the plates to the fractured bone segments. Furthermore, both types of bone plates may be somewhat curved in order to accommodate the cross-section shape of the particular bone. Compression plates are typically thicker and the include interior holes are typically "compression holes" having either one or two ramps which extend longitudinally toward the center of the hole from the outer to the inner surface of the plate. The compression holes cause the bone plate to move longitudinally relative to the bone screws used to secured the plate, as the screws are tightened. The one-third semi-tubular plates are relatively thinner and typically include straight-through holes without the longitudinally extending ramps.

Both compression plates and one-third semi-tubular plates have been widely and successfully used to stabilize bone fractures. However, the implantation of either type of plate may be problematic for the surgeon in certain instances.

The bone fracture is approached through a standard incision. Soft tissue such as periosteum, muscle, arteries and veins are partially stripped from the bone to allow visualization of the area and to allow temporary placement of bone clamps and implantation of the bone plate for plates. The surgeon commonly faces situations in which he or she struggles to achieve alignment of the fractured bones with the use of bone clamps, only to have to remove the same implants securing the reduction in order to position and attach the bone plate. After the structure is reduced, the bone segments must then be held in place to allow removal of the clamps to permit placement of the bone plate. In some instances, the fracture may be secured by placing a bone screw across the fracture site.

During the healing process, a so-called sintering of the fracture will occur, which may entail a shortening of the bone in this region. In order to make sure that the fixation with the aid of the osteosynthesis plate may follow this, the screws must move relative to the plate in the elongated holes. Between the screwhead and the hole, however, there is essentially only a point contact place taking place. By virtue of the high surface pressure at the contact points, the screwhead digs itself more and more into the material of the plate and causes an extraordinary high coefficient of frictional adhesion which practically permits the relative movement.

In the past, various patents have issued relating to the use of such bone plate assemblies.

U.S. Pat. Nos. 2,443,363 and 2,486,303 are early bone plate apparatus. U.S. Pat. No. 2,443,363 teaches a bone plate having a plurality of elongated slots through which bone screws are secured. The elongated slots extend on each side of the fracture. U.S. Pat. No. 2,486,303 teaches a curved bone plate also having a plurality of elongated slots on each side of the fracture. Bone screws are inserted into each of the elongated slots.

U.S. Pat. No. 3,604,414, issued on Sep. 14, 1971 to Borges et al., describes an osteosynthesis plate of two-piece construction having a toothed rack system to enable sliding movement of the two pieces in a direction to move the plate pieces in a direction to achieve the greatest approximation of a fractured bone so as to facilitate the joining of the fracture of the bone. The plates are secured to the fragments of the bone by screw members and a tool for moving the plates toward each other.

U.S. Pat. No. 3,659,595, issued on May 2, 1972 to E. J. Haboush, describes a compensation plate for bone fractures including slotted holes on one side of the fracture and slotted holes on the opposite side of the fracture. In particular, a pair of plates are employed whereby one of the plates is located on one side of the fracture and the other plate is located on the other side of the fracture. The elongated holes of each of the plates are overlapped with each other so that the surgical screw can be inserted therein.

U.S. Pat. No. 4,597,497, issued on Sep. 18, 1990 to Hoogland, et al., describes a device for osteosynthesis which includes an elongated bone plate and an elongated slide plate adapted to be fitted to the outside of the bone plate. Several longitudinally spaced elongated holes for the reception of bone screws are provided in one longitudinal portion only of the bone plate. The other longitudinal portion of the bone plate is provided with circular holes and the elongated slide plate is provided with several spaced circular holes.

U.S. Pat. No. 5,234,431, issued on Aug. 10, 1993, teaches a bone plate arrangement consisting of a bone plate with at least one through-opening and a bone screw to be introduced into the through-opening. The bone screw is held to the bone plate by means of a sleeve, which can be fixed in the through-opening of the bone plate independently of the screw.

U.S. Pat. No. 5,951,557, issued on Sep. 17, 1999 to D. W. Luter, describes another type of bone plate having first and second end portions longitudinally spaced from one another and an intermediate portion extending between the end portions. The plate includes at least one interior hole formed in the intermediate portion for receiving a fastener, such as a bone screw, to attach the plate to the fractured bone. A plurality of apertures are formed in the plate, with each of the end portions including at least one of the apertures which extends through the plate from the upper surface to the lower surface for receiving a bone screw.

U.S. Pat. No. 6,280,445, issued on Aug. 28, 2001 to Morrison et al., describes a multi-axial bone anchor system as used for spinal implants. The system includes an elongated member, one or more bone anchor assemblies, and stabilizer members that are fitted within the elongated member. A bone anchor is attached to a bone, and the elongated member and stabilizer are fitted over the bone anchor.

Unfortunately, with these bone fixation plates, where elongated slots are provided, it is common for the surgeon to install the screw in the wrong portion of the elongated slot. As a result, when the bones tend to compress toward each other, the limit of movement of one bone portion with respect to the other bone portion is limited by the length of the slot and the distance from which the screw (as initially installed) moves to a wall of the elongated slot. Since it is important for the bone to compress upon itself for proper healing, a certain amount of movement must be accomplished by the use of the bone plate. Where overlapping plates are employed, it is often difficult for the surgeon to achieve the proper overlapping of the bone plate so that the circular holes can be placed in a proper position with respect to the elongated holes.

It is an object of the present invention to provide a bone plate assembly which effectively assists the healing process by allowing the bone fracture portions to compress toward each other.

It is another object of the present invention to provide a bone plate assembly which assures that the surgeon installs the screw in a proper location.

It is another object of the present invention to provide a bone plate assembly whereby the relationship between the bone plate and the bone tightens as the compression occurs.

It is a further object of the present invention to provide a bone plate assembly which is easy to use, relatively inexpensive and easy to manufacture.

These and other objects and advantages of the present invention will become apparent from a reading of the attached specification and appended claims.

BRIEF SUMMARY OF THE INVENTION

The present invention is a bone fixation plate comprising a plate having a first set of openings and a second set of openings, and a plurality of clip members removably fitted respectively into the plurality of the openings of the second set of openings. The first set of openings is a plurality of, circular through holes extending through the plate transverse to the longitudinal axis of the plate. The second set of openings comprises a plurality of elongated holes extending through the plate transverse to the longitudinal axis of the plate. The plurality of clip members within each of the plurality of elongated holes fills a space within the elongated hole so as to allow for the accurate placement of a bone screw therein.

In the present invention, the first set of openings is formed on one side of a center of the plate and the second set of openings is formed on an opposite side of the center of the plate. Each of the first set of openings has a generally constant diameter through the depth of the holes. Each of the plurality of elongated holes has a length dimension which is greater than a width dimension of the hole. Each of the clip members in the respective elongated holes defines an opening of a similar diameter as the constant diameter of the circular through hole. Each of the plurality of through holes has a chamfered area adjacent one side of the plate. Each of the plurality of elongated holes also includes a chamfered portion adjacent the one side of the plate.

Each of the plurality of clip members has a surface extending outwardly of one side of the plate. Each of the plurality of elongated holes has a tapered slot formed in a wall thereof. The plate includes a top side and a bottom side. The tapered slot tapers toward the bottom side in a direction toward the median of the plate.

In the present invention, a first set of screws are respectively received within the first set of openings. A second set of screws are respectively received within the second set of openings. Each of the plurality of clip members resides in removable juxtaposition against the respective screws of the second set of screws.

The present invention is also a method of fixing a break between a first bone portion and a second bone portion comprising the steps of: (1) placing a plate across the break such that the first set of openings is positioned adjacent the first bone portion and the second set of openings is positioned adjacent the second bone portion; (2) positioning a plurality of clip members in the respective elongated areas of the second set of openings such that the clip members define a screw-receiving space within each elongated hole; (3) applying screws through the first set of openings so as to engage the first bone portion; (4) applying screws into the screw receiving space of the second set of opening so as to engage the second bone portion; and (5) removing the plurality of clip members from the second set of openings.

In the present invention, the screws within the elongated holes of the second set of opening slide toward the center of the plate as the first bone portion compresses toward the second bone portion. Also, in the method of the present invention, a tapered slot can be formed in each of the plurality of elongated holes of the second set of openings, a protrusion can be formed on a shank of the bone screws, and the protrusion is fitted into the tapered slot so that the protrusion moves along the tapered slot as the first bone portion compresses toward the second bone portion. In the present invention, the step of removing the clip members includes lifting an edge of each of the plurality of clip members.

DETAILED DESCRIPTION OF THE INVENTION

Figure 1:
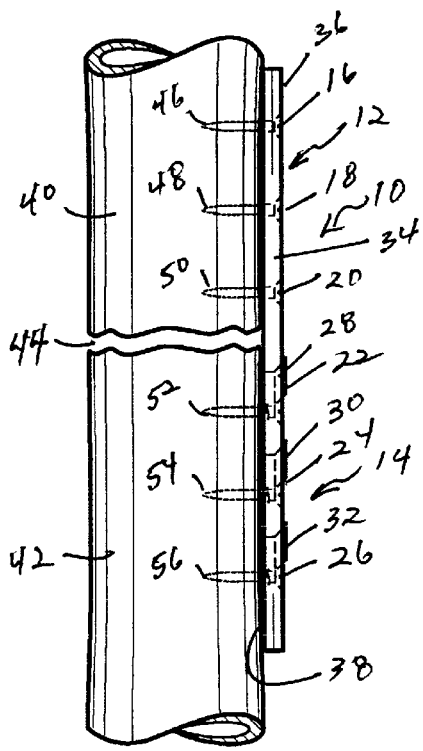
FIG. 1 is a side view showing the installation of the bone plate assembly of the present invention.

Referring to FIG. 1, there is shown at the bone plate assembly in accordance with the teachings of the present invention. The bone plate assembly 10 includes a first set of openings 12 and a second set of openings 14. In particular, the first set of openings 12 includes a first circular hole 16, a second circular hole 18 and a third circular hole 20. The second set of openings 14 includes a first elongated hole 22, a second elongated hole 24 and a third elongated hole 26. A plurality of clip members are fitted within the elongated holes 22, 24 and 26. The first clip member 28 is installed within the first elongated hole 28. A second clip member 30 is installed within the second elongated hole 24. A third clip member 32 is installed within the third elongated hole 26.

In FIG. 1, it can be seen that the bone plate 34 has a top side 36 and a bottom side 38. The bottom side 38 is placed in proximity to the outer surface of bone portions 40 and 42. A fracture 44 is shown between the bone portions 40 and 42. So as to secure the bone plate 34 to the bone portions 40 and 42, screws 46, 48 and 50 are installed through the circular holes 16, 18 and 20, respectively. Similarly, bone screws 52, 54 and 56 are installed in the respective elongated holes 22, 24 and 26. Each of the clip members 28, 30 and 32 will define a space through which the bone screws 52, 54 and 56 can be installed.

Figure 2:
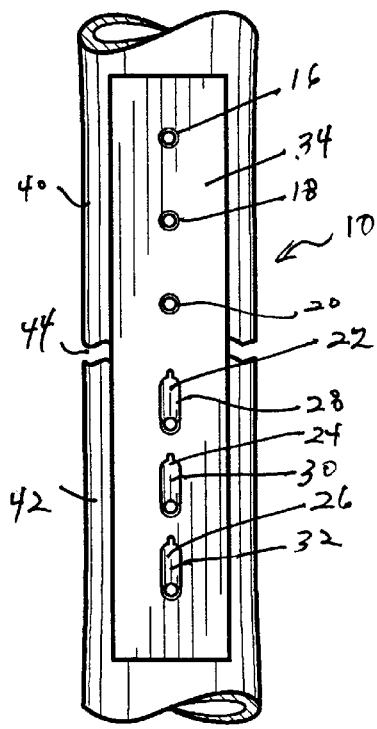
FIG. 2 is a frontal view showing the initial installation of the bone plate assembly of the present invention.

FIG. 2 further shows the configuration of the bone plate assembly 10 of the present invention. Bone plate assembly 10 is shown as including bone plate 34 as having a generally rectangular configuration. In FIG. 2, it can be seen that the circular holes 16, 18 and 20 are particularly illustrated as associated with the first bone portion 40. Similarly, the elongated through holes 22, 24 and 26 are positioned so as to reside on the opposite side of the fracture 44 on the bone portion 42. It can be seen in FIG. 2 that the circular holes 16, 18 and 20 define a space through which the respective screws 46, 48 and 50 can be inserted. Similarly, the clip members 28, 30 and 32 serve to define a space through which the bone screws 52, 54 and 56 can be inserted.

Importantly, it can be seen that the screw-receiving openings associated with each of the elongated holes 22, 24 and 26 allows the screw to be placed at the bottom of each of the elongated holes. As such, the clip members 28, 30 and 32 will assure to the surgeon that the bone screw is installed in the proper location within the slot. The present invention facilitates maximum movement of the first bone portion toward the second bone portion 42 so that the fracture 44 can heal.

Figure 3:
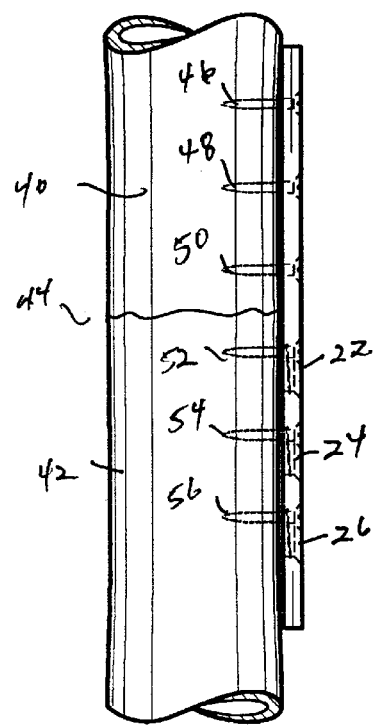
FIG. 3 is a side view showing the healing of the fracture and its relationship to the bone plate assembly of the present invention.

In FIG. 3, the fracture 44 has suitably healed so that the first bone portion 40 is in juxtaposition against the second bone portion 42. In FIG. 3, it can be seen that the screws 46, 48 and 50 remain in the same position as in FIG. 1. However, the bone screws 52, 54 and 56 have drifted along the elongated slots 22, 24 and 26 so that the second bone portions 42 can move with respect to the first bone portion 40. The movement of the bone segments 52, 54 and 56 within the respective elongated holes 22, 24 and 26 can be accomplished by the removal of the respective clip members 28, 30 and 32 from the respective elongated holes.

Figure 4:
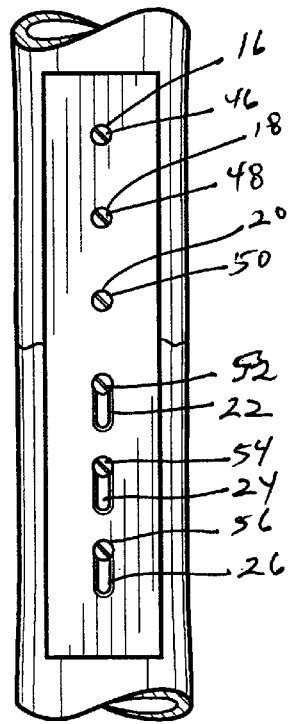
FIG. 4 is a frontal view showing the healed fracture and the relationship to the bone plate assembly of the present invention.

In FIG. 4, it can be seen how the bone screws 46, 48 and 50 are properly installed within the circular holes 16, 18 and 20. Similarly, in FIG. 4, the bone screws 52, 54 and 56 are now residing in the upper end of the elongated holes 22, 24 and 26. In FIG. 4, the elongated holes 22, 24 and 26 have a length dimension which is greater than a width dimension.

Figure 5:
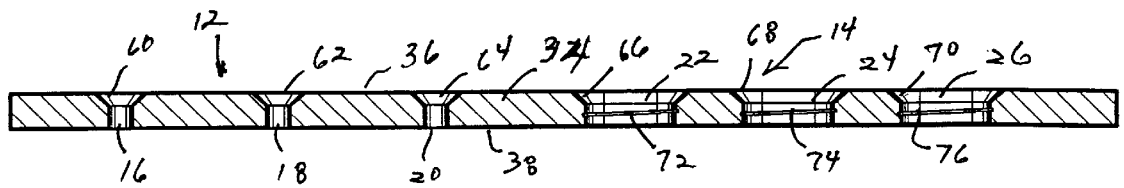
FIG. 5 is a cross-sectional view of the bone plate in accordance with the teachings of the present invention.

FIG. 5 shows an isolated view of the bone plate 34. Bone plate 34 has an outer surface 36 and an inner surface 38. The first set of openings 12 is located on one side of the center of the bone plate 34 from the second set of openings 14. In FIG. 5, each of the first set of openings 12 include circular through holes 16, 18 and 20. A chamfered area 60, 62 and 64 provided adjacent to this outer side 36. Chamfered areas 60, 62 and 64 will accommodate the head of the bone screw.

In FIG. 5, the arrangement of the elongated slots 22, 24 and 26 is particularly shown. Each of the elongated holes 22, 24 and 26 includes chamfered areas 66, 68 and 70, respectively, for accommodating the head of the bone screw received therein. Importantly, tapered slots 72, 74 and 76 will extend across the length dimension and is formed into a wall of the respective elongated holes 22, 24 and 26. Tapered slots 72, 74 and 76 will allow a bone screw inserted therein to tighten slightly as the first portion 40 compresses against the second bone portion 42.

Figure 6:
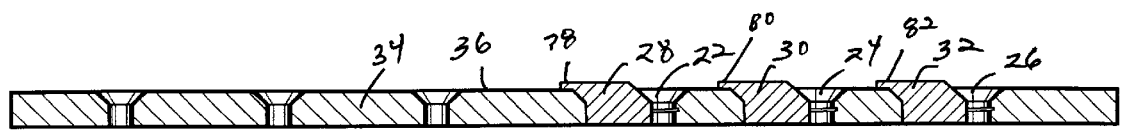
FIG. 6 shows a cross-sectional view of the bone plates of FIG. 5 with the clip members installed within the elongated holes.

In FIG. 6, there is particularly shown the clip members 28, 30 and 32 as positioned within the respective elongated holes 22, 24 and 26. Each of the clip members 28, 30 and 32 has a respective surface 78, 80 and 82 which extends outwardly of the outer surface 36 of the bone plate 34. As a result, each of the clip members 28, 30 and 32 can be removed by lifting up on this outwardly extending edge. Each of the clip members 28, 30 and 32 will define an area whereby the respective screws 52, 54 and 56 can be installed so that the head of the screw will reside within the chamfered areas 66, 68 and 70.

Figure 7:
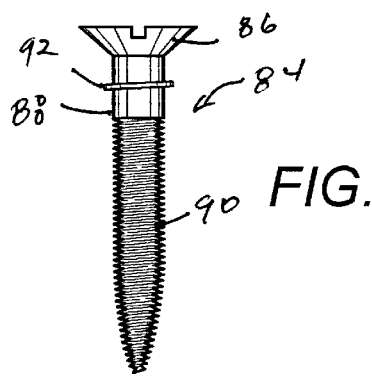
FIG. 7 is an isolated view of a bone screw associated with the present invention.

FIG. 7 shows a bone screw 84 having a head 86, a shank portion 88 and a bone-engaging threaded area 90. A protrusion 92 is formed on the shank portion 88 suitable for engagement with the tapered slots 72, 74 and 76. The protrusion 92 can take various forms, such as simple protrusions or an annular rib extending around the shank portion 88. The head 86 is suitably tapered so as to fit within the chamfered areas of the bone plate 34.

Figure 8:
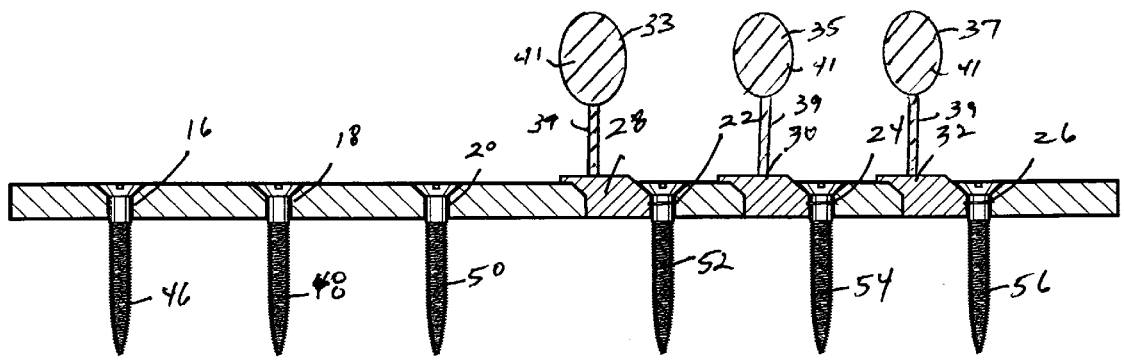
FIG. 8 shows the bone screws as installed within each of the first and second sets of openings associated with the bone plates of the present invention.

FIG. 8 shows each of the bone screws 46, 48 and 50 as installed within the circular holes 16, 18 and 20. Similarly, FIG. 8 shows the bone screws 52, 54 and 56 as installed within the elongated holes 22, 24 and 26. The respective clip members 28, 30 and 32 create an area whereby the screws 22, 24 and 26 can be properly installed. Each of the clip members 28, 30 and 32 has a respective tab element 33, 35 and 37 extending therefrom. The tab elements 33, 35 and 37 allow the surgeon to easily grasp the clip members in an area well away from the bone. Each of the tab elements 33, 35 and 37 has a shank portion 39 and a grasping surface 41. The grasping surface 41 is an end of the shank portion 39 opposite the clip members 28, 30 and 32.

The foregoing disclosure and description of the invention is illustrative and explanatory thereof. Various changes in the details of the illustrated construction may be made within the scope of the appended claims without departing from the true spirit of the invention. The present invention should only be limited by the following claims and their legal equivalents.

I claim:

1. A bone fixation plate comprising:

a plate having a first set of openings and a second set of openings, said first set of openings comprising a plurality of circular holes extending through said plate transverse to a longitudinal axis of said plate, said second set of openings comprising a plurality of elongated holes extending through said plate transverse to said longitudinal axis of said plate; and a plurality of clip members removably fitted respectively into said plurality of elongated through holes, each of said plurality of clip members filling a portion of a space within a respective elongated hole, each of said plurality of clip members having a surface extending outwardly of one side of said plate.

2. The bone fixation plate of claim 1, said each of said first set of openings formed on one side of a center of said plate, said second set of openings formed on an opposite side of the center of said plate.

3. The bone fixation plate of claim 1, each of said plurality of circular holes having a generally constant diameter, each of said plurality of elongated holes having a length dimension greater than a width dimension thereof.

4. The bone fixation plate of claim 3, each of said plurality of clip members within a respective elongated hole of said plurality of elongated holes defining an opening of a similar diameter as the constant diameter of the circular hole of said first set of openings.

5. The bone fixation plate of claim 3, each of said plurality of circular holes having a chamfered area adjacent one side of said plate, each of said plurality of elongated holes having a chamfered portion adjacent said one side of said plate.

6. The bone fixation plate of claim 3, said surface of each of said clip members being a tab element extending outwardly therefrom.

7. The bone fixation plate of claim 6, said tab element having a shank portion connected to the clip members and a grasping surface formed at an end of said shank portion opposite the clip element.

8. A bone fixation assembly comprising:
a plate having a first set of openings and a second set of openings, said second set of openings being a plurality of elongated through holes extending through said plate transverse to a longitudinal axis of said plate;
a plurality of clip members removably fitted respectively into said plurality of elongated through holes, each of said plurality of clip members filling a portion of a space in the elongated hole;
a first set of screws respectively received within said first set of openings;
a second set of screws respectively received within said second set of openings, said plurality of clip members residing in removable juxtaposition against respective screws of said second set of screws.

9. The bone fixation assembly of claim 8, each of said clip members defining an opening of a similar diameter as the diameter of each of said first set of openings.

10. The bone fixation assembly of claim 8, said first set of openings having a chamfered area adjacent one side of said plate, each of said plurality of elongated holes having a chamfered portion adjacent said one side of said plate, each screw of said first set of screws having a head with a wider diameter than a remainder of the screw, said head residing within said chamfered area.

11. The bone fixation assembly of claim 8, each of said plurality of elongated holes having a tapered slot formed in a wall thereof, each of said second set of screws having a protrusion suitable for fitting within said tapered slot.

12. The bone fixation assembly of claim 8, each of said first and second set of screws having a length dimension greater than a thickness of said plate.

13. The bone fixation assembly of claim 8, each of said plurality of clip members having a tapered surface adjacent a top side of said plate, each of said second set of screws having a head with a surface residing against said tapered surface.

14. The bone fixation assembly of claim 8, each of said plurality of clip members having a surface extending outwardly of one side of said plate.

15. The bone fixation assembly of claim 8, each of said second set of screws being slidable within the respective elongated holes of said plurality of elongated holes.

16. A method of fixing a break between a first bone portion and a second bone portion comprising:
placing a plate across the break, said plate having a plurality of circular holes positioned adjacent the first bone portion, said plate having a plurality of elongated holes positioned adjacent the second bone portion;
positioning a plurality of clip members in respective elongated holes of said plurality of elongated holes, said plurality of clip members each defining a screw receiving space within the elongated holes;
applying screws through said plurality of circular holes so as to engage said first bone portion;
applying screws into said screw receiving space of each of said plurality of elongated holes so as to engage said second bone portion; and
removing said plurality of clip members from respective elongated holes of said plurality of elongated holes.

17. The method of claim 16, further comprising:
sliding said screws in said plurality of elongated holes as the first bone portion progresses toward the second bone portion.

18. The method of claim 16, further comprising:
forming a tapered slot in each of said plurality of elongated holes;
forming a protrusion on a shank of said screws that are applied into said plurality of elongated holes; and
fitting said protrusion into said tapered slot, said protrusion moving along said tapered slot as the first bone portion progresses toward the second bone portion.

19. The method of claim 16, said step of removing comprising:
lifting an edge of each of said plurality of clip members, said edge residing on an outer surface of the said plate.

* * * * *